United States Patent
Nam

(10) Patent No.: US 6,680,076 B2
(45) Date of Patent: Jan. 20, 2004

(54) NATURAL TEAS FOR INCREASING STAMINA AND METHOD OF PREPARING THE SAME

(76) Inventor: Jong Hyun Nam, 3850 Wilshire Blvd., #345 Los Angeles, CA (US) 90010

( * ) Notice: Subject to any disclaimer, the term of this patent is extended or adjusted under 35 U.S.C. 154(b) by 0 days.

(21) Appl. No.: 10/095,683

(22) Filed: Mar. 11, 2002

(65) Prior Publication Data

US 2003/0086983 A1 May 8, 2003

(30) Foreign Application Priority Data

Mar. 30, 2001 (KR) ......................... 2001-16987

(51) Int. Cl.⁷ ........................ A61K 35/78; A01N 65/00
(52) U.S. Cl. .................. 424/725; 424/746; 424/773; 424/779
(58) Field of Search ................... 424/725, 773, 424/746, 779

(56) References Cited

U.S. PATENT DOCUMENTS 6,399,116 B1 * 6/2002 Xiu ........................... 424/773

* cited by examiner

Primary Examiner—Herbert J. Lilling
(74) Attorney, Agent, or Firm—Galgano & Burke

(57) ABSTRACT

The present invention relates to natural teas and a method of preparing the same, which is effective in increasing sexual ability or stamina. According to the present invention, there are provided relatively inexpensive natural teas in the form of liquid natural teas, powders, segments, or concentrated extracts, in which *Rhodiola sachalinensis*, and *Cuscutae Semens* and/or *Torilidis Fructus*; *Rhodiola sachalinensis* and a parasitic plant; or a mixture of all the above herbs is contained as principal elements, to which at least one species selected from the group consisting of *Alnus japonica, Salviae Radix, Polyglae Radix*, schizandra and lycium is optionally added. Where the natural teas of the present invention are drunk two times one day, an excellent effect of increasing stamina can be obtained.

27 Claims, No Drawings

NATURAL TEAS FOR INCREASING STAMINA AND METHOD OF PREPARING THE SAME

BACKGROUND OF THE INVENTION

1. Field of the Invention

The present invention relates generally to natural teas for increasing stamina and a method of preparing the same. More particularly, the present invention relates to natural teas having an effect of increasing stamina, and a method of preparing the same, in which an extract from a parasitic plant, an extract from *Polyglae Radix,* an extract from *Torilidis Fructus,* an extract from *Salviae Radix,* an extract from *Alnus japonica*, or a combination thereof, is added to an extract from *Rhodiola sachalinensis* A. Bor.

2. Description of the Prior Art

The human with excellent intellectuality recognizes a sex not only as a simple way for preservation of the species but also an important way for operating happy and pleasant family life. Today, operation of happy and pleasant family life is regarded as significantly affecting domestic happiness, although it is not essential therefor. As domestic happiness is linked with social vital power and national prosperity, its importance cannot be overlooked. Particularly in males, increasing stamina or sexual ability has been desired from ancient times, and strong stamina has been also regarded as the masculine symbol. However, it is reported through many literatures that sexual ability of the human, particularly the male, is seriously decreased from various viewpoints including a reduction in spermatozoon number, due to contamination of air, water resources and soil according to highly advanced industry, contamination of foods caused by excessive use of agricultural chemicals and treatment with preservative agents, instant foods, acute stress in harsh competition society, lack of exercise according to a busy life, and the like.

Meanwhile, as the material richness is increased, and particularly an opportunity to be exposed to the sexual stimulation is highly increased due to development of mass media and an increase in netizen number, a concern about a sex is more increased.

For this reason, it can be said that a male of the present time is under unbalanced circumstances where the sexual ability is generally reduced while a concern about a sex is increased.

Such circumstances cause some of males to intake all foods, which are known to be good for health although being disgust foods. For this reason, wild animals which must be protected are captured, resulting in the situation where an ecosystem is destroyed. Meanwhile, although a tendency to recover the decreased sexual ability by stimulation with a drug is increased, there are side effects which are necessarily accompanied with the drug itself. For example, although a drug for improving sexual function is sold all over the world, it is reported that the drug can be fatal in a hypertensive or a patient with a heart disease. Also, it has a problem of expensive costs.

Furthermore, there is a case where alcohol is used for a sexual life from a point where alcohol somewhat relaxes strain of a nervous system. However, although alcohol can be somewhat useful for the sexual life at very small amounts, it significantly reduces sexual ability at increased amounts. In addition, if alcohol is habitually ingested, a disorder of neurility and a disorder of sexual function can be induced by alcoholism.

As a result, health foods have been demanded from the past, which are effective in increasing sexual ability or stamina of males.

SUMMARY OF THE INVENTION

A first object of the present invention is to provide natural teas having an effect of increasing stamina.

A second object of the present invention is to provide natural teas having an effect of increasing a motility of spermatozoons.

A third object of the present invention is to provide natural teas having a stamina-increasing effect at low costs.

A fourth object of the present invention is to provide a method of preparing the natural teas according to the first and second objects of the present invention.

According to a first preferred aspect of the present invention, the above objects can be achieved by natural teas and a method of preparing the same, which comprises an extract from *Rhodiola sachalinensis* A. Bor and an extract from a parasitic plant, as basic elements.

According to a second preferred aspect of the present invention, the above objects can be achieved by natural teas and a method of preparing the same, which comprises an extract from *Rhodiola sachalinensis* A. Bor, and an extract from *Cuscutae Semens* and/or *Torilidis Fructus,* as basic elements.

According to a third preferred aspect of the present invention, the above objects can be achieved by natural teas and a method of preparing the same, which comprises an extract from *Rhodiola sachalinensis* A. Bor, an extract from a parasitic plant and an extract from *Alnus japonica*, as basic elements.

According to a fourth preferred aspect of the present invention, the above objects can be achieved by natural teas and a method of preparing the same, which comprises an extract from *Rhodiola sachalinensis* A. Bor, an extract from *Cuscutae Semens* and/or an extract from *Torilidis Fructus,* as basic elements, to which an extract from *Salviae Radix,* an extract from *Polyglae Radix,* an extract from lycium, an extract from schizandra, or a combination thereof is added as an optional element.

DETAILED DESCRIPTION OF THE PREFERRED EMBODIMENTS

The present invention relates to natural teas and a method of preparing the same, which comprises *Rhodiola sachalinensis* A. Bor as a first raw material, a parasitic plant, *Cuscutae Semens* and/or *Torilidis Fructus* as a second raw material, *Salviae Radix, Polyglae Radix* and *Alnus japonica* as a third raw material, and lycium and/or schizandra as a fourth raw material. The present invention is achieved by mixing of the first and second raw materials. The third and fourth raw materials are optional in the present invention.

*Rhodiola sachalinensis* A. Bor which is used as the first raw material in the present invention belongs to Rhodiola of Crassulaceae, and contains salidrosides and their glycosides, as main components. From results of recent studies in China, it is reported that *Rhodiola sachalinensis* A. Bor has a pharmacological action equal to ginseng while it exhibits no side effects. Although a total herb of *Rhodiola sachalinensis* A. Bor may be used, it is preferred to use roots of *Rhodiola sachalinensis* A. Bor. In Chinese medicine, *Rhodiola sachalinensis* A. Bor is used for the treatment or prevention of nervous breakdown, senile cardiac muscle breakdown, anemia, arthritis, diabetes, hypotension, amnesia, amblyopia, tinnitus, and declines in energy, etc.

The content of the extract of *Rhodiola sachalinensis* A. Bor in the stamina increasing natural teas of the present invention is in the range of 10 to 95% by weight, and preferably 40 to 80% by weight.

Hereinafter, the parasitic plant, *Cuscutae Semens* and *Torilidis Fructus* will be successively described.

The parasitic plant includes *Cistanchis deserticola* Y. C. Ma, *Orobanche coerulescens* Steph, and *Lathraea japonica* Miq. In the present invention, *Cistanche deserticola* Y. C. Ma is preferably used.

*Cistanche deserticola* Y. C. Ma is a plant of Orobanchaceae and used in a peeled state. In Chinese medicine, this herb is known to have a hypotensive action, a confortantive action, a defecation action, and a salivation accelerating action.

*Orobanche coerulescens* Steph is a plant of Orobanchaceae, and its total herb has been used for medical purposes as a tonic and a sexual ability-increasing agent in folks.

*Lathraea japonica* Miq. is a plant belonging to Orobanchaceae. In Chinese medicine, its total herb is dried in the sun at the bloom and used as a tonic, a sexual ability-increasing agent, fluor, and a cardiotonic agent, etc.

The content of the extract of *Cistanche deserticola* Y. C. Ma, *Orobanche coerulescens* Steph, *Lathraea japonica* Miq. or a combination thereof in the stamina increasing natural teas of the present invention is in the range of 5 to 90% by weight, and preferably 10 to 60% by weight.

*Cuscutae Semens* is a seed of *Cuscuta chinensis* Lam. which is a plant of Convolvulaceae. In Chinese medicine, this herb is powdered and used as a nutrient, a sexual ability-increasing agent, and a tonic, and for the improvement of impotence, nocturnal pollution and lumbago. In Dongeubogam, this herb is reported to be effective in increasing energy and in improving diabetes.

*Torilidis Fructus* is a fruit of *Cnidium monieri* Cuss. which is a plant of Umbelliferae. In Chinese medicine, it is used to support Yang-Ki and to improve a symptom of uterine vital energy deficiency and cold.

The content of the extract of the *Cuscutae Semens, Torilidis Fructus,* or a combination thereof in the natural teas of the present invention is in the range of 5 to 90% by weight, and preferably 10 to 60% by weight.

Hereinafter, *Salviae Radix, Polyglae Radix* and *Alnus japonica*, which are used as the third raw material, an optional element, in the present invention, will be described.

*Salviae Radix* is a root of *Salvia miltiorrhza* Bge. belonging to Labiatae. In Chinese medicine, this herb is reported as having vasodilation, antibacterial, sedation and analgesic actions.

*Polygalae Radix* is a root of *Polygala tenuifolia* Willd. which is a plant belonging to Polygalaceae. In Chinese medicine, it is known as stabilizing the mind, improving amnesia and insomnia, and having expectorant and antitussive actions.

*Alnus japonica* is known to be rich in tannin at its fruit, leave, root and stem and effective in protecting the stomach mucosa. Further details on *Aldus japonica* are described in Korean Patent No. 181168 owned by this applicant.

The content of the extract of *Salviae Radix, Polyglae Radix, Alnus japonica* or a combination thereof in the natural teas of the present invention is in the range of 5 to 85% by weight, and preferably 10 to 60% by weight, if any.

Hereinafter, schizandra and/or lycium which are used as the fourth raw material in the present invention will be described.

Schizandra is a fruit of *Maximowiczia chinensis*. In Chinese medicine, this herb is known to improve the visual power, and to contain organic acids and saponin, etc. which are effective in recovering from fatigue. Lycium is a fruit of Chinese matrimony vine. In Collection of Oriental Drugs, Lycium is described as having tonic, face-whitening, and tranquilizer effects. If any, the content of the schizandra and/or lycium in the natural teas of the present invention is in the range of 5 to 80% by weight, and preferably 10 to 60% by weight.

In the present invention, water, ethanol or a mixture thereof is used as an extractant. Extracting conditions are not critical to the present invention, but extraction may be carried out at room temperature to 100° C. Generally, the extraction may be carried out at room temperature to 45° C. for 1 to 48 hours.

As used herein, the term "extract" is intended to include an extraction liquid, and a powder formed by drying the extraction liquid to a moisture content of 5 to 20%, using a drying means, such as lyophilization, air-dry, warm heat-drying, hot air drying, infrared drying, or irradiation with electromagnetic wave, etc., as well as a consistent extract having a moisture content of more than 20%.

The present invention will hereinafter be described in further detail by examples. It should however be borne in mind that the present invention is not limited to or by the examples.

EXAMPLE 1

(1) Step 1: Preparation of Extract from *Rhodiola sachalinensis* A. Bor

A root of *Rhodiola sachalinensis* A. Bor was washed, dried and then finely chopped. Then, 8 g of the resulting herb was extracted in a mixture of 130 cc of 95% ethanol and 330 cc of water at 35° C. for 4 hours in an extractor. Ethanol was volatilized to obtain 300 cc of an extract of *Rhodiola sachalinensis* A. Bor.

(2) Step 2: Preparation of Extract from *Cistanche deserticola* Y. C. Ma (Parasitic Plant)

A total herb of *Cistanche deserticola* Y. C. Ma was washed, dried and then finely chopped. Then, 2 g of the resulting herb was extracted in a mixture of 130 cc of 95% ethanol and 330 cc of water at 35° C. for 4 hours in an extractor. Ethanol was volatilized to obtain 300 cc of an extract of *Cistanche deserticola* Y. C. Ma.

(3) Step 3: Preparation of Natural Tea 300 cc of the extract of *Rhodiola sachalinensis* A. Bor obtained in Step 1 was mixed with 300 cc of the extract of *Cistanche deserticola* Y. C. Ma obtained in Step 2, thereby preparing a natural tea of the present invention.

EXAMPLE 2

(1) Step 1: Preparation of Extract from *Rhodiola sachalinensis* A. Bor 300 cc of an extract of *Rhodiola sachalinensis* A. Bor. was obtained in the same manner as in Step 1 of Example 1.

(2) Step 2: Preparation of Extract from *Cistanche deserticola* Y. C. Ma 300 cc of an extract of *Cistanche deserticola* Y. C. Ma. was obtained in the same manner as in Step 2 of Example 1.

(3) Step 3: Preparation of Extract from *Salviae Radix*

*Salviae Radix* was washed, dried and then finely chopped. Then, 2 g of the resulting herb was extracted in a mixture of 130 cc of 95% ethanol and 330 cc of water at 35° C. for 4 hours in an extractor. Ethanol was volatilized to obtain 300 cc of an extract of *Salviae Radix*.

(4) Step 4: Preparation of Natural Tea 300 cc of the extract of *Rhodiola sachalinensis* A. Bor obtained in Step 1 was mixed with 150 cc of the extract of *Cistanche deserticola* Y. C. Ma obtained in Step 2 and 150 cc of the extract of *Salviae Radix* obtained in Step 3, thereby preparing a natural tea of the present invention in the same manner as in Example 1.

EXAMPLE 3

(1) Step 1: Preparation of Extract from *Rhodiola sachalinensis* A. Bor 300 cc of an extract of *Rhodiola sachalinensis* A. Bor. was obtained in the same manner as in Step 1 of Example 1, except that 6 g of a root of *Rhodiola sachalinensis* A. Bor. was used.

(2) Step 2: Preparation of Extract from *Cistanche deserticola* Y. C. Ma 300 cc of an extract of *Cistanche deserticola* Y. C. Ma. was obtained in the same manner as in Step 2 of Example 1, except that 6 g of a total herb of *Cistanche deserticola* Y. C. Ma was used.

(3) Step 3: Preparation of Extract from *Polyglae Radix*

*Polyglae Radix* was washed, dried and then finely chopped. Then, 2 g of the resulting material was extracted in a mixture of 130 cc of 95% ethanol and 330 cc of water at 35° C. for 4 hours in an extractor. Ethanol was volatilized to obtain 300 cc of an extract of *Polyglae Radix*.

(4) Step 4: Preparation of Natural Tea 250 cc of the extract of *Rhodiola sachalinensis* A. Bor obtained in Step 1 was mixed with 300 cc of the extract of *Cistanche deserticola* Y. C. Ma obtained in Step 2 and 150 cc of the extract of *Polyglae Radix* obtained in Step 3, thereby preparing a natural tea of the present invention in the same manner as in Example 1.

EXAMPLE 4

(1) Step 1: Preparation of Extract from *Rhodiola sachalinensis* A. Bor 300 cc of an extract of *Rhodiola sachalinensis* A. Bor. was obtained in the same manner as in Step 1 of Example 1.

(2) Step 2: Preparation of Extract from *Cistanche deserticola* Y. C. Ma 300 cc of an extract of *Cistanche deserticola* Y. C. Ma. was obtained in the same manner as in Step 2 of Example 1.

(3) Step 3: Preparation of Extract from *Cuscutae Semens*

*Cuscutae Semens* was washed, dried and then crushed. Then, 2 g of the resulting material was extracted in a mixture of 130 cc of 95% ethanol and 330 cc of water at 35° C. for 4 hours in an extractor. Ethanol was volatilized to obtain 300 cc of an extract of *Cuscutae Semens*.

(4) Step 4: Preparation of Extract from *Salviae Radix*

300 cc of an extract of *Salviae Radix* was obtained in the same manner as in Step 3 of Example 2.

(5) Step 5: Preparation of Extract from *Polyglae Radix*

300 cc of an extract of *Polyglae Radix* was obtained in the same manner as in Step 3 of Example 3.

(6) Step 6: Preparation of Natural Tea 150 cc of the extract of *Rhodiola sachalinensis* A. Bor obtained in Step 1, 300 cc of the extract of *Cistanche deserticola* Y. C. Ma obtained in Step 2, 300 cc of the extract of *Cuscutae Semens* obtained in Step 3, 75 cc of the extract of *Salviae Radix,* and 75 cc of the extract of *Polyglae Radix* obtained in Step 5, were mixed with each other, thereby preparing a natural tea of the present invention in the same manner as in Example 1.

EXAMPLE 5

(1) Step 1: Preparation of Extract from *Rhodiola sachalinensis* A. Bor 300 cc of an extract of *Rhodiola sachalinensis* A. Bor. was obtained in the same manner as in Step 1 of Example 1.

(2) Step 2: Preparation of Extract from *Cistanche deserticola* Y. C. Ma 300 cc of an extract of *Cistanche deserticola* Y. C. Ma. was obtained in the same manner as in Step 2 of Example 1.

(3) Step 3: Preparation of Extract from *Cuscutae Semens*

300 cc of an extract of *Cuscutae Semens* was obtained in the same manner as in Step 3 of Example 4.

(4) Step 4: Preparation of Extract from *Torilidis Fructus*

*Torilidis Fructus* was washed, dried and then crushed. Then, 2 g of the resulting material was extracted in a mixture of 130 cc of 95% ethanol and 330 cc of water at 35° C. for 4 hours in an extractor. Ethanol was volatilized to obtain 300 cc of an extract of *Torilidis Fructus*.

(5) Step 5: Preparation of Extract from *Salviae Radix*

300 cc of an extract of *Salviae Radix* was obtained in the same manner as in Step 3 of Example 2.

(6) Step 6: Preparation of Extract from *Polyglae Radix*

300 cc of an extract of *Polyglae Radix* was obtained in the same manner as in Step 3 of Example 3.

(7) Step 7: Preparation of Natural Tea 75 cc of the extract of *Rhodiola sachalinensis* A. Bor obtained in Step 1, 300 cc of the extract of *Cistanche deserticola* Y. C. Ma obtained in Step 2, 150 cc of the extract of *Cuscutae Semens* obtained in Step 3, 150 cc of *Torilidis Fructus* obtained in Step 4, 75 cc of the extract of *Salviae Radix* obtained in Step 5, and 75 cc of the extract of *Polyglae Radix* obtained in Step 6, were mixed with each other, thereby preparing a natural tea of the present invention in the same manner as in Example 1.

EXAMPLE 6

(1) Step 1: Preparation of Extract from *Rhodiola sachalinensis* A. Bor 320 cc of an extract of *Rhodiola sachalinensis* A. Bor. was obtained in the same manner as in Step 1 of Example 1.

(2) Step 2: Preparation of Extract from *Cistanche deserticola* Y. C. Ma 300 cc of an extract of *Cistanche deserticola* Y. C. Ma. was obtained in the same manner as in Step 2 of Example 1.

(3) Step 3: Preparation of Extract from Root of *Alnus japonica*

A root of *Alnus japonica* was washed, dried and then finely chopped. Then, 5 g of the resulting material was extracted in a mixture of 130 cc of 95% ethanol and 330 cc of water at 35° C. for 4 hours in an extractor. Ethanol was volatilized to obtain 300 cc of an extract of a root of *Alnus japonica*.

(4) Step 7: Preparation of Natural Tea 300 cc of the extract of *Rhodiola sachalinensis* A. Bor obtained in Step 1, 150 cc of the extract of *Cistanche deserticola* Y. C. Ma obtained in Step 2, and 60 cc of the *Alnus japonica* root extract obtained in Step 3, were mixed with each other, thereby preparing a natural tea of the present invention in the same manner as in Example 1.

EXAMPLE 7

(1) Step 1: Preparation of Extract from *Rhodiola sachalinensis* A. Bor 280 cc of an extract of *Rhodiola sachalinensis* A. Bor. was obtained in the same manner as in Step 1 of Example 1.

(2) Step 2: Preparation of Extract from *Cuscutae Semens*

300 cc of an extract of *Cuscutae Semens* was obtained in the same manner as in Step 3 of Example 4, except that 4 g of *Cuscutae Semens* was used.

(3) Step 7: Preparation of Natural Tea 280 cc of the extract of *Rhodiola sachalinensis* A. Bor obtained in Step 1, and 300 cc of the extract of *Cuscutae Semens* obtained in Step 2 were mixed with each other, thereby preparing a natural tea of the present invention.

EXAMPLE 8

(1) Step 1: Preparation of Extract from *Rhodiola sachalinensis* A. Bor 300 cc of an extract of *Rhodiola sachalinensis* A. Bor. was obtained in the same manner as in Step 1 of Example 7.

(2) Step 2: Preparation of extract from *Cuscutae Semens*

300 cc of an extract of *Cuscutae Semens* was obtained in the same manner as in Step 3 of Example 4.

(3) Step 4: Preparation of Extract from *Torilidis Fructus*

300 cc of an extract of *Torilidis Fructus* was obtained in the same manner as in Step 4 of Example 5.

(4) Step 4: Preparation of Natural Tea 150 cc of the extract of *Rhodiola sachalinensis* A. Bor obtained in Step 1, 300 cc of the extract of *Cuscutae Semens* obtained in Step 2, and 300 cc of *Torilidis Fructus* obtained in Step 3 were mixed with each other, thereby preparing a natural tea of the present invention in the same manner as in Example 1.

EXAMPLE 9

(1) Step 1: Preparation of Extract from *Rhodiola sachalinensis* A. Bor 300 cc of an extract of *Rhodiola sachalinensis* A. Bor. was obtained in the same manner as in Step 1 of Example 7.

(2) Step 2: Preparation of Extract from *Cuscutae Semens*

300 cc of an extract of *Cuscutae Semens* was obtained in the same manner as in Step 3 of Example 4.

(3) Step 3: Preparation of Extract from *Torilidis Fructus*

300 cc of an extract of *Torilidis Fructus* was obtained in the same manner as in Step 4 of Example 5.

(4) Step 4: Preparation of Extract from *Salviae Radix*

300 cc of an extract of *Salviae Radix* was obtained in the same manner as in Step 3 of Example 2.

(5) Step 5: Preparation of Natural Tea 200 cc of the extract of *Rhodiola sachalinensis* A. Bor obtained in Step 1, 300 cc of the extract of *Cuscutae Semens* obtained in Step 2, 150 cc of *Torilidis Fructus* obtained in Step 3, and 300 cc of the extract of *Salviae Radix* obtained in Step 4, were mixed with each other, thereby preparing a natural tea of the present invention in the same manner as in Example 5.

EXAMPLE 10

(1) Step 1: Preparation of Extract from *Rhodiola sachalinensis* A. Bor 200 cc of an extract of *Rhodiola sachalinensis* A. Bor. was obtained in the same manner as in Step 1 of Example 9.

(2) Step 2: Preparation of Extract from *Cistanche deserticola* Y. C. Ma 300 cc of an extract of *Cistanche deserticola* Y. C. Ma. was obtained in the same manner as in Step 2 of Example 1.

(3) Step 3: Preparation of Extract from *Cuscutae Semens*

300 cc of an extract of *Cuscutae Semens* was obtained in the same manner as in Step 3 of Example 4.

(4) Step 4: Preparation of Extract from *Salviae Radix*

300 cc of an extract of *Salviae Radix* was obtained in the same manner as in Step 4 of Example 9.

(5) Step 7: Preparation of Natural Tea 200 cc of the extract of *Rhodiola sachalinensis* A. Bor obtained in Step 1, 150 cc of the extract of *Cistanche deserticola* Y. C. Ma obtained in Step 2, 150 cc of *Cuscutae Semens* obtained in Step 3, and 300 cc of the extract of *Salviae Radix* obtained in Step 4, were mixed with each other, thereby preparing a natural tea of the present invention in the same manner as in Example 9.

EXAMPLE 11

(1) Step 1: Preparation of Extract from *Rhodiola sachalinensis* A. Bor 300 cc of an extract of *Rhodiola sachalinensis* A. Bor. was obtained in the same manner as in Step 1 of Example 1.

(2) Step 2: Preparation of Extract from *Torilidis Fructus*

300 cc of an extract of *Torilidis Fructus* was obtained in the same manner as in Step 3 of Example 9.

(3) Step 3: Preparation of Extract from *Salviae Radix*

300 cc of an extract of *Salviae Radix* was obtained in the same manner as in Step 4 of Example 4.

(4) Step 4: Preparation of Extract from *Polyglae Radix*

300 cc of an extract of *Polyglae Radix* was obtained in the same manner as in Step 5 of Example 4.

(5) Step 5: Preparation of Natural Tea 250 cc of the extract of *Rhodiola sachalinensis* A. Bor obtained in Step 1, 150 cc of *Torilidis Fructus* obtained in Step 2, 75 cc of the extract of *Salviae Radix* obtained in Step 3, and 75 cc of the extract of *Polyglae Radix* obtained in Step 4, were mixed with each other, thereby preparing a natural tea of the present invention in the same manner as in Example 10.

EXAMPLE 12

(1) Step 1: Preparation of Extract from *Rhodiola sachalinensis* A. Bor 300 cc of an extract of *Rhodiola sachalinensis* A. Bor. was obtained in the same manner as in Step 1 of Example 1.

(2) Step 2: Preparation of Extract from *Cistanche deserticola* Y. C. Ma 300 cc of an extract of *Cistanche deserticola* Y. C. Ma. was obtained in the same manner as in Step 2 of Example 10.

(3) Step 3: Preparation of Extract from *Torilidis Fructus*

300 cc of an extract of *Torilidis Fructus* was obtained in the same manner as in Step 2 of Example 11.

(4) Step 4: Preparation of Extract from *Salviae Radix*

300 cc of an extract of *Salviae Radix* was obtained in the same manner as in Step 3 of Example 11.

(5) Step 5: Preparation of Extract from *Polyglae Radix*

300 cc of an extract of *Polyglae Radix* was obtained in the same manner as in Step 4 of Example 11.

(6) Step 6: Preparation of Natural Tea 200 cc of the extract of *Rhodiola sachalinensis* A. Bor obtained in Step 1, 200 cc of the extract of *Cistanche deserticola* Y. C. Ma obtained in Step 2, 150 cc of *Torilidis Fructus* obtained in Step 3, 75 cc of the extract of *Salviae Radix* obtained in Step 4, and 75 cc of the extract of *Polyglae Radix* obtained in Step 5, were mixed with each other, thereby preparing a natural tea of the present invention in the same manner as in Example 11.

EXAMPLE 13

(1) Step 1: Preparation of Extract from *Rhodiola sachalinensis* A. Bor 300 cc of an extract of *Rhodiola sachalinensis* A. Bor. was obtained in the same manner as in Step 1 of Example 1, except that 9 g of *Rhodiola sachalinensis* A. Bor. was used.

(2) Step 2: Preparation of Extract from *Cistanche deserticola* Y. C. Ma 300 cc of an extract of *Cistanche deserticola* Y. C. Ma. was obtained in the same manner as in Step 2 of Example 10, except that a total herb of *Cistanche deserticola* Y. C. Ma. was used in a state where it was not peeled.

(3) Step 3: Preparation of Extract from *Cuscutae Semens*

300 cc of an extract of *Cuscutae Semens* was obtained in the same manner as in Step 3 of Example 10.

(4) Step 4: Preparation of Natural Tea 300 cc of the extract of *Rhodiola sachalinensis* A. Bor obtained in Step 1, 75 cc of the extract of *Cistanche deserticola* Y. C. Ma obtained in Step 2, and 75 cc of the extract of *Cuscutae Semens* obtained in Step 3, were mixed with each other, thereby preparing a natural tea of the present invention.

EXAMPLE 14

(1) Step 1: Preparation of Extract from *Rhodiola sachalinensis* A. Bor 280 cc of an extract of *Rhodiola sachalinensis* A. Bor. was obtained in the same manner as in Step 1 of Example 1.

(2) Step 2: Preparation of Extract from *Torilidis Fructus*

300 cc of an extract of *Torilidis Fructus* was obtained in the same manner as in Step 2 of Example 11.

(3) Step 3: Preparation of Extract from stem of *Alnus japonica*

A stem of *Alnus japonica* was washed, dried and then finely chopped. Then, 6 g of the resulting material was extracted in the same manner as in Step 3 of Example 6, thereby obtaining 300 cc of an extract of a stem of *Alnus japonica*.

(4) Step 4: Preparation of Natural Tea 300 cc of the extract of *Rhodiola sachalinensis* A. Bor obtained in Step 1, 150 cc of *Torilidis Fructus* obtained in Step 2, and 60 cc of the stem extract of *Alnus japonica* obtained in Step 3, were mixed with each other, thereby preparing a natural tea of the present invention in the same manner as in Example 11.

EXAMPLE 15

A natural tea of the present invention was prepared in the same manner as in Example 14, except that 150 cc of an extract of *Salviae Radix* obtained in the same manner as Step 3 of Example 2 and 250 cc of an extract of *Rhodiola sachalinensis* A. Bor obtained in Example 14 were used.

EXAMPLE 16

A natural tea of the present invention was prepared in the substantially same manner as in Example 12, except that 75 cc of an extract of *Torilidis Radix* obtained in Example 12 and 75 cc of an extract of *Cuscutae Semens* obtained according to Step 3 of Example 13 were used.

EXAMPLE 17

A natural tea of the present invention was prepared in the substantially same manner as in Example 16, except that 200 cc of an extract of *Rhodiola sachalinensis* A. Bor, 150 cc of an extract of *Torilidis Radix,* 150 cc of an extract of *Cuscutae Semens* were used and 60 cc of an extract of an *Alnus japonica* obtained in the substantially same manner as Example were used.

EXAMPLE 18

A natural tea of the present invention was prepared in the substantially same manner as in Example 17, except that 80 cc of an extract of *Rhodiola sachalinensis* A. Bor, and 75 cc of an extract of schizandra were used. The extract of schizandra used in this Example was prepared as follows: schizandra was washed, dried and then crushed. Then, 5 g of the resulting material was extracted in a mixture of 130 cc of 95% ethanol and 330 cc of water at 35° C. for 4 hours in an extractor. Ethanol was volatilized to obtain 300 cc of an extract of schizandra.

EXAMPLE 19

A natural tea of the present invention was prepared in the substantially same manner as Example 16, except that 300 cc of an extract of *Rhodiola sachalinensis* A. Bor, 40 cc of an extract of *Salviae Radix* and 40 cc of an extract of *Polyglae Radix* were used.

EXAMPLE 20

A natural tea of the present invention was prepared in the substantially same manner as in Example 6, except that 200 cc of an extract of *Rhodiola sachalinensis* A. Bor, 75 cc of an extract of schizandra obtained in Example 18, and 75 cc of an extract of lycium were used. The extract of lycium used in this Example was prepared as follows: lycium was washed, dried and then crushed. Then, 5 g of the resulting material was extracted in a mixture of 130 cc of 95% ethanol and 330 cc of water at 35° C. for 4 hours in an extractor. Ethanol was volatilized to obtain 300 cc of an extract of lycium.

EXAMPLE 21

(1) Step 1: Preparation of Extract from *Rhodiola sachalinensis* A. Bor

A total herb of *Rhodiola sachalinensis* A. Bor was washed, dried and then finely chopped. Then, 8 g of the resulting herb was extracted in a mixture of 130 cc of 95% ethanol and 330 cc of water at 35° C. for 6 hours in an extractor. Ethanol was volatilized to obtain 200 cc of an extract of *Rhodiola sachalinensis* A. Bor.

(2) Step 2: Preparation of Extract from *Cistanche deserticola* Y. C. Ma

A total herb of *Cistanche deserticola* Y. C. Ma was washed, dried and then finely chopped. Then, 2 g of the resulting material was extracted in a mixture of 130 cc of 95% ethanol and 330 cc of water at 35° C. for 6 hours in an extractor. Ethanol was volatilized to obtain 180 cc of an extract of *Cistanche deserticola* Y. C. Ma.

(3) Step 3: Preparation of Extract from *Cuscutae Semens*

*Cuscutae Semens* was washed, dried and then crushed. Then, 2 g of the resulting material was extracted in a mixture of 130 cc of 95% ethanol and 330 cc of water at 35° C. for 6 hours in an extractor. Ethanol was volatilized to obtain 200 cc of an extract of *Cuscutae Semens*.

(4) Step 4: Preparation of Extract from *Torilidis Fructus*

*Torilidis Fructus* was washed, dried and then crushed. Then, 2 g of the resulting material was extracted in a mixture of 130 cc of 95% ethanol and 330 cc of water at 35° C. for 6 hours in an extractor. Ethanol was volatilized to obtain 200 cc of an extract of *Torilidis Fructus*.

(5) Step 5: Preparation of Extract from *Salviae Radix*

*Salviae Radix* was washed, dried and then finely chopped. Then, 2 g of the resulting material was extracted in a mixture of 130 cc of 95% ethanol and 330 cc of water at 35° C. for 6 hours in an extractor. Ethanol was volatilized to obtain 200 cc of an extract of *Salviae Radix*.

(6) Step 5: Preparation of Extract from *Polyglae Radix*

*Polyglae Radix* was washed, dried and then finely chopped. Then, 2 g of the resulting material was extracted in a mixture of 130 cc of 95% ethanol and 330 cc of water at 35° C. for 6 hours in an extractor. Ethanol was volatilized to obtain 180 cc of an extract of *Salviae Radix*.

(7) Step 7: Preparation of Extract from leave/stem/root of *Alnus japonica*

A mixture of leave/stem/root of *Alnus japonica* was optionally uniformly taken, washed, dried and then finely chopped. Then, 1.5 g (0.5 g for each portion) of the resulting material was extracted in a mixture of 130 cc of 95% ethanol and 330 cc of water at 35° C. for 6 hours in an extractor. Ethanol was volatilized to obtain 150 cc of a mixed extract of leave/stem/root of *Alnus japonica*.

(8) Step 8: Preparation of Extract From Schizandra

Schizandra was washed, dried and then crushed. Then, 2 g of the resulting material was extracted in a mixture of 130 cc of 95% ethanol and 330 cc of water at 35° C. for 6 hours in an extractor. Ethanol was volatilized to obtain 180 cc of an extract of schizandra.

(9) Step 9: Preparation of Extract From Lycium

Lycium was washed, dried and then crushed. Then, 2 g of the resulting material was extracted in a mixture of 130 cc of 95% ethanol and 330 cc of water at 35° C. for 6 hours in an extractor. Ethanol was volatilized to obtain 180 cc of an extract of lycium.

(10) Step 3: Preparation of Natural Tea 50 cc of the extract of *Rhodiola sachalinensis* A. Bor, 90 cc of the extract of *Cistanche deserticola* Y. C. Ma, 100 cc of the extract of *Cuscutae Semens,* 100 cc of the *Torilidis Fructus,* 100 cc of the extract of *Salviae Radix,* 90 cc of the extract of *Polyglae Radix,* 100 cc of the mixed extract of leave/stem/root of *Alnus japonica,* 90 cc of the extract of schizandra, and 90 cc of the extract of lycium, were mixed with each other, thereby preparing a natural tea of the present invention.

EXAMPLE 22

A natural tea of the present invention was prepared according to the substantially same procedure and method as in Example 21, except that 150 cc of the extract of *Rhodiola sachalinensis* A. Bor obtained in Step 1 of Example 21 was used, and the extract of *Salviae Radix* in Step 5, the extract of *Alnus japonica* in Step 7, the extract of schizandra in Step 8 and the extract of lycium in Step 9, were not used.

EXAMPLE 23

A natural tea of the present invention was prepared according to the substantially same procedure and method as in Example 21, except that 130 cc of the extract of *Rhodiola sachalinensis* A. Bor obtained in Step 1 of Example 21 was used, and the extract of *Salviae Radix* in Step 5, the extract of schizandra in Step 8 and the extract of lycium in Step 9, were not used.

EXAMPLE 24

A natural tea of the present invention was prepared according to the substantially same procedure and method as in Example 23, except that the extract of schizandra obtained in Step 8 of Example 21 was used instead of the extract of *Alnus japonica.*

EXAMPLE 25

A natural tea of the present invention was prepared according to the substantially same procedure and method as in Example 23, except that the extract of lycium obtained in Step 9 of Example 21 was used instead of the extract of *Alnus japonica.*

EXAMPLE 26

A natural tea of the present invention was prepared according to the substantially same procedure and method as in Example 24, except that 200 cc of the extract of *Cuscutae Semens* was used and the extract of *Cistanche deserticola* Y. C. Ma. was not used.

EXAMPLE 27

A natural tea of the present invention was prepared according to the substantially same procedure and method as in Example 26, except that 100 cc of the extract of *Cuscutae Semens* and 200 cc of the extract of *Torilidis Fructus* were used.

EXAMPLE 28

A natural tea of the present invention was prepared according to the substantially same procedure and method as in Example 25, except that *Lathraea japonica* was used instead of *Cistanche deserticola* Y. C. Ma.

EXAMPLE 29

A natural tea of the present invention was prepared according to the same procedure and method as in Example 22, except that 100 cc of the extract of *Salviae Radix* obtained in Step 5 of Example 21 was further used.

EXAMPLE 30

A natural tea of the present invention was prepared according to the substantially same procedure and method as in Example 27, except that 100 cc of the extract of *Torilidis Fructus* and 180 cc of the extract of schizandra were used.

EXAMPLE 31

A natural tea of the present invention was prepared according to the substantially same procedure and method as in Example 30, except that 90 cc of the extract of schizandra and 90 cc of the extract of lycium obtained in Step 9 of Example 21 were used.

EXAMPLE 32

A natural tea of the present invention was prepared according to the substantially same procedure and method as in Example 31, except that 100 cc of the extract of *Salviae Radix* obtained in Step 5 of Example 21 was used instead of the extract of schizandra.

EXAMPLE 33

A natural tea of the present invention was prepared by mixing 125 cc of the extract of *Rhodiola sachalinensis* A. Bor obtained in Step 1 of Example 21, 90 cc of the extract of *Cistanche deserticola* Y. C. Ma in Step 2, 100 cc of the extract of *Torilidis Fructus* in Step 4, 100 cc of the extract of *Salviae Radix* in Step 5, 100 cc of the mixed extract of leave/stem/root of *Alnus japonica* in Step 7, and 90 cc of the extract of schizandra Step 8.

EXAMPLE 34

A natural tea of the present invention was prepared by mixing 200 cc of the extract of *Rhodiola sachalinensis* A. Bor obtained in Step 1 of Example 21, 90 cc of the extract obtained by treatment of *Orobanche coerulescens* Steph. instead of *Cistanche deserticola* Y. C. Ma at the same amount and condition as in Step 2 of Example 21, and 100 cc of the extract of *Cuscutae Semens* in Step 3 of Example 21.

EXAMPLE 35

A natural tea of the present invention was prepared by mixing 150 cc of the extract of *Rhodiola sachalinensis* A. Bor obtained in Step 1 of Example 21, 90 cc of the extract obtained by treatment of *Lathraea japonica* instead of *Cistanche deserticola* Y. C. Ma at the same amount and condition as in Step 2 of Example 21, and 100 cc of the extract of *Cuscutae Semens* in Step 3 of Example 21, and 100 cc of *Torilidis Fructus* in Step 4 of Example 21.

EXAMPLE 36

A natural tea of the present invention was prepared according to the substantially same procedure and method as Example 35, except that 120 cc of the extract of *Rhodiola sachalinensis* A. Bor was used, 90 cc of the extract obtained by treatment of *Cistanche deserticola* Y. C. Ma instead of *Lathraea japonica* at the same amount and condition was used, and 90 cc of the extract of lycium obtained in Step 9 of Example 21 was further mixed.

EXAMPLE 37

A natural tea of the present invention was prepared according to the substantially same procedure and method as Example 35, except that 90 cc of the extract obtained by treatment of *Cistanche deserticola* Y. C. Ma instead of *Lathraea japonica* at the same amount and condition was used.

EXAMPLE 38

A natural tea of the present invention was prepared according to the substantially same procedure and method as Example 21, except that 80 cc of the extract of *Rhodiola sachalinensis* A. Bor was used, and the extract of *Alnus japonica* in Step 7 was not used.

EXAMPLE 38

A natural tea of the present invention was prepared according to the substantially same procedure and method as Example 21, except that 80 cc of the extract of *Rhodiola sachalinensis* A. Bor was used, and the extract of *Alnus japonica* in Step 7 was not used.

EXAMPLE 39

A natural tea of the present invention was prepared according to the substantially same procedure and method as Example 21, except that 50 cc of the extract of *Rhodiola sachalinensis* A. Bor and 180 cc of the extract of *Cistanche deserticola* Y. C. Ma obtained in Step 2 was used, and the extract of *Cuscutae Semens* in Step 3 was not used.

EXAMPLE 40

A natural tea of the present invention was prepared according to the substantially same procedure and method as Example 21, except that 120 cc of the extract of *Rhodiola sachalinensis* A. Bor and 180 cc of the extract obtained by use of 3 g of *Cistanche deserticola* Y. C. Ma in Step 2 were used, and the extracts of *Alnus japonica*, schizandra and lycium in Steps 7–9 were not used.

EXAMPLE 41

A natural tea of the present invention was prepared according to the substantially same procedure and method as Example 40, except that 100 cc of the extract of *Torilidis Fructus* obtained in Example 21 was used instead of the extract of *Cuscutae Semens,* and 100 cc of the extract of *Salviae Radix* obtained in Example 21 was used instead of the extract of *Polyglae Radix.*

EXAMPLE 42

A natural tea of the present invention was prepared according to the substantially same procedure and method as Example 41, except that 180 cc of the extract obtained by use of 2 g of *Cistanche deserticola* Y. C. Ma was used, and 90 cc of the extracts of *Polyglae Radix* obtained in Example 21 was further used.

EXAMPLE 43

A natural tea of the present invention was prepared according to the basically same procedure and method as Example 42, except that 100 cc of the extract of *Cuscutae Semens* obtained in Example 21 was used instead of 100 cc of *Torilidis Fructus.*

EXAMPLE 44

A natural tea of the present invention was prepared according to the substantially same procedure and method as Example 21, except that 120 cc of the extract of *Rhodiola sachalinensis* A. Bor, 180 cc of the extract of *Cistanche deserticola* Y. C. Ma, 100 cc of the extract of *Torilidis Fructus* and 200 cc of the extract of *Alnus japonica* were used, and the extracts of *Cuscutae Semens, Salviae Radix, Polyglae Radix,* schizandra and lycium were not used.

EXAMPLE 45

A natural tea of the present invention was prepared according to the basically same procedure and method as Example 44, except that 100 cc of the extract of *Torilidis Fructus* was used and 100 cc of the extract of *Salviae Radix* obtained in Example 21 was used instead of the extract of *Alnus japonica.*

EXAMPLE 46

A natural tea of the present invention was prepared according to the substantially same procedure and method as Example 21, except that 170 cc of the extract of *Rhodiola sachalinensis* A. Bor, 90 cc of the extract of *Cistanche deserticola* Y. C. Ma, 100 cc of *Torilidis Fructus* and 100 cc of the extract of *Polyglae Radix* were used and the extracts of *Cuscutae Semens, Salviae Radix, Alnus japonica,* schizandra and lycium were not used.

EXAMPLE 47

A natural tea of the present invention was prepared according to the substantially same procedure and method as Example 46, except that 100 cc of the extract of *Salviae Radix* was used instead of 90 cc of the extract of Polyglae Radix.

EXAMPLE 48

A natural tea of the present invention was prepared according to the substantially same procedure and method as Example 47, except that 100 cc of the extract of *Alnus japonica* and 100 cc of the extract of schizandra were used instead of the extracts of *Torilidis Fructus* and *Salviae Radix,* respectively.

EXAMPLE 49

A natural tea of the present invention was prepared according to the substantially same procedure and method as Example 45, except that 175 cc of the extract of *Rhodiola sachalinensis* was used and the extract of *Cistanche deserticola* Y. C. Ma was not used.

EXAMPLE 50

A natural tea of the present invention was prepared according to the substantially same procedure and method as

EXAMPLE 51

A natural tea of the present invention was prepared according to the substantially same procedure and method as Example 47, except that 200 cc of the extract of *Rhodiola sachalinensis* A. Bor was used and the extract of *Salviae Radix* was not used.

Example 42, except that 175 cc of the extract of *Rhodiola sachalinensis* was used and the extract of *Cistanche deserticola* Y. C. Ma was not used.

EXAMPLE 52

A natural tea of the present invention was prepared according to the substantially same procedure and method as Example 51, except that the extracts of *Cistanche deserticola* Y. C. Ma and *Torilidis Fructus* were used and 100 cc of the extract of *Cuscutae Semens* and 90 cc of the extract of *Polyglae Radix* were further used which were obtained in Example 21.

EXAMPLE 53

A natural tea of the present invention was prepared according to the substantially same procedure and method as Example 50, except that 200 cc of the extract of *Rhodiola sachalinensis*, 50 cc of the extract of *Salviae Radix* and 45 cc of the extract of *Polyglae Fructus* were used.

EXAMPLE 54

A natural tea of the present invention was prepared according to the substantially same procedure and method as Example 49, except that 200 cc of the extract of *Rhodiola sachalinensis*, 50 cc of the extract of *Torilidis Fructus* and 45 cc of the extract of *Salviae Radix* were used.

EXAMPLE 55

A natural tea of the present invention was prepared according to the substantially same procedure and method as Example 37, except that 200 cc of the extract of *Rhodiola sachalinensis*, 50 cc of the extract of *Cuscutae Semens* and 45 cc of the extract of *Salviae Radix* were used.

EXAMPLE 56

A natural tea of the present invention was prepared according to the substantially same procedure and method as Example 38, except that 100 cc of the extract of *Rhodiola sachalinensis* A. Bor and 180 cc of the extract of *Cistanche deserticola* Y. C. Ma were used.

EXAMPLE 57

A natural tea of the present invention was prepared according to the substantially same procedure and method as Example 38, except that 100 cc of the extract of *Rhodiola sachalinensis* A. Bor and 100 cc of the extract obtained by carrying out extraction as in Example 21 using only leaves of *Alnus japonica*.

EXAMPLE 58

A natural tea of the present invention was prepared according to the substantially same procedure and method as Example 57, except that the extracts of *Cuscutae Semens* and leaves of *Alnus japonica* were used and 90 cc of the extract of schizandra and 90 cc of the extract of lycium were further used which are obtained in Example 21.

EXAMPLE 59

A natural tea of the present invention was prepared according to the substantially same procedure and method as Example 58, except that the extract of *Polyglae Radix* was used and 100 cc of the extract of *Cuscutae Semens* was further used which are obtained in Example 21.

EXAMPLE 60

A natural tea of the present invention was prepared according to the substantially same procedure and method as Example 42, except that 100 cc of the extract of *Rhodiola sachalinensis* A. Bor and 200 cc of *Torilidis Fructus* were used.

In Examples of the present invention as described above, the extraction was uniformly carried out using the mixture of 95% ethanol and water as an extractant. However, the present invention is not limited only to use of this extractant, and use of a suitable diluted alcohol solvent and use of appropriate combinations of solvents is also within the scope of the present invention. For example, extraction can be carried out using water depending on raw materials, and some raw materials can be extracted using only ethanol. If necessary, other organic solvents may also be used, provided they can be completely removed by boiling.

The products from Examples as described above were tested in various manners, and it was consequently found that the natural tea prepared using 10 to 90% by weight, and preferably 40 to 80% by weight, of the extract of *Rhodiola sachalinensis* A. Bor and 5 to 90% by weight, and preferably 10 to 60% by weight, of the extract of *Cuscutae Semens* and/or *Torilidis Fructus*, as basic elements, or the natural tea prepared using 10 to 95% by weight, and preferably 40 to 80% by weight, of *Rhodiola sachalinensis* A. Bor and 5 to 90% by weight, and preferably 10 to 60% by weight, of the extract of the parasitic plants, as basic elements, is effective in improving stamina. It was also found that where 5 to 85% by weight, and preferably 10 to 65% by weight, of the extract of *Salviae Radix, Polyglae Radix* and/or *Alnus japonica*, and 5 to 80% by weight, and preferably 10 to 60% by weight, of the extract of lycium and/or schizandra is added to the basic elements, the stamina increasing effect of the natural tea of the present invention can be further improved.

The extract as described above was extracted from an individual raw material or a mixture of raw materials using ethanol or water, and an extraction ratio was preferably 40 to 120 cc/g. Furthermore, although an extraction time varies depending on whether ethanol is used or not, a ratio of ethanol to water, and temperature, etc., it should be understood that these parameters are not critical to the present invention and are only optional particulars.

In the above Examples, there were described the methods of preparing the natural tea of the present invention by extraction with ethanol or water. However, even when tea components are drunk which are obtained by a method in which raw materials is introduced into an autoclave at the mixing ratio as described in the above Examples, steamed, finely crushed, lyophilized, put in a tea bag, dipped into boiling water and then extracted, similarly to a method of preparing a green teas and the like, the same effect as that of the natural teas prepared in the above Examples can be obtained. Also, it is understood that this method is within the scope of the present invention.

Furthermore, although experiments using stems, leaves and roots of *Alnus japonica* were carried out and an test using fruits of *Alnus japonica* was not carried out, it should be understood that use of the fruits of *Alnus japonica* exhibits the same effect as the stems, leaves and roots of *Alnus japonica* and thus is also within the scope of the present invention.

In the natural teas according to the present invention, addition of additional ingredients or microingredients such as sweetening agents or perfumes, etc, which are used in the art in order to improve taste or flavor, etc., is possible and is also within the scope of the present invention.

Comparative Example 1

*Rhodiola sachalinensis* A. Bor which is the first raw material for the natural tea of the present invention was washed and finely chopped. 10 g of the resulting plant was introduced into a mixture of 500 cc of 95% ethanol and 500 cc of water and extracted at 55° C. for 6 hours. Ethanol was volatilized, thereby obtaining 450 cc of an extract of *Rhodiola sachalinensis* A. Bor which is used as Comparative Example 1.

Comparative Example 2

*Cistanche deserticola* Y. C. Ma which is the second raw materials for the natural tea of the present invention was peeled, washed and finely chopped. 10 g of the resulting herb was introduced into a mixture of 500 cc of 95% ethanol and 500 cc of water and extracted at 55° C. for 6 hours. Ethanol was volatilized, thereby obtaining 430 cc of an extract of *Cistanche deserticola* Y. C. Ma which is used as Comparative Example 2.

Comparative Example 3

2 g of *Cistanche deserticola* Y. C. Ma, 2 g of *Cuscutae Semens* and 2 g of *Torilidis Fructus,* which are the second materials for the natural tea of the present invention, were washed, finely chopped and mixed. The resulting herb mixture into a mixture of 500 cc of 95% ethanol and 500 cc of water and extracted at 55° C. for 6 hours. Ethanol was volatilized, thereby obtaining 430 cc of an extract of *Cistanche deserticola* Y. C. Ma which is used as Comparative Example 3.

Test Example 1

In order to measure a stamina increasing effect resulted from use of the natural tea of the present invention, the natural tea of the present invention and the natural tea of Comparative Examples were drunk by 181 males in their forties to seventies, after taking breakfast and before retiring, for 30 days, at 140 cc each time, and examined for satisfiability. When providing the natural teas, announcement indicating that 50% of the provided natural teas are the effective real while the rest of the natural teas are the ineffective false was made, so that coherence caused by the placebo effect is minimized. The male volunteers were subjected to the blind test. The results are shown in Table 1 below.

TABLE 1

| Examples | Classification | Forties | Fifties | Sixties | Seventies |
|---|---|---|---|---|---|
| Comparative Example 1 | Effective | 1 | 0 | 0 | 0 |
|  | Ineffective | 9 | 10 | 10 | 10 |
| Comparative Example 2 | Effective | 0 | 0 | 0 | 0 |
|  | Ineffective | 10 | 10 | 10 | 10 |

TABLE 1-continued

| Examples | Classification | Forties | Fifties | Sixties | Seventies |
|---|---|---|---|---|---|
| Comparative Example 3 | Effective | 0 | 1 | 0 | 0 |
|  | Ineffective | 10 | 9 | 10 | 10 |
| Example 1 | Effective | 4 | 2 | 1 | 0 |
|  | Ineffective | 6 | 8 | 9 | 10 |
| Example 8 | Effective | 3 | 1 | 0 | 0 |
|  | Ineffective | 7 | 9 | 10 | 10 |
| Example 10 | Effective | 4 | 3 | 1 | 0 |
|  | Ineffective | 6 | 7 | 9 | 0 |
| Example 21 | Effective | 10 | 9 | 8 | 8 |
|  | Ineffective | 0 | 1 | 2 | 2 |
| Example 29 | Effective | 9 | 7 | 5 | 5 |
|  | Ineffective | 1 | 3 | 5 | 5 |
| Example 38 | Effective | 8 | 8 | 6 | 6 |
|  | Ineffective | 2 | 2 | 4 | 4 |
| Example 57 | Effective | 9 | 8 | 6 | 5 |
|  | Ineffective | 1 | 2 | 4 | 5 |

From Table 1, it was found that effects are also obtained only with a combination of *Rhodiola sachalinensis* A. Bor, and *Cistanche deserticola* Y. C. Ma, *Cuscutae Semens* and/or *Torilidis Fructus,* although there is a difference depending on the state of health of the male volunteers, the stamina property or the mental state. However, it is believed that, where all the above herbs are mixed or *Polyglae Radix, Salviae Radix, Alnus japonica*, schizandra and/or lycium are further added thereto, significant cumulative synergistic effects are obtained.

Test Example 2

Animal Test of Natural Tea of the Present Invention

Changes in testicular weight and sperm motility were measured, which are obtained when the natural teas for increasing stamina according to the present invention (natural teas of Examples 21, 29 and 57) are supplied to test animals in a drink form.

A test was carried out under the following conditions:

Test time: 9 weeks;

Test groups: four groups consisting of a control group (pure water), and natural tea drinks according to Examples 21, 29 and 57 of the present invention;

Test diets: Purina diets for white rats are supplied;

Test drinks: fresh water, or drinks in which natural teas of Examples 21, 29 and 59 of the present invention are diluted at 1:12 (v/v) and which are stored in a refrigerator, are supplied every day;

Test animals: 40 three-week-old S. D. rats were purchased and divided into four groups each consisting of 10 rats; and Measured items: growth rate, weights of liver and testicle, and sperm motility and concentration.

The growth rate was recorded as % increase of body weight per day, and the weight of sperm was recorded as the total weight of the right and left side.

The test results are as follows:

Although a statistical difference between growth rates of the test groups was not exhibited, the groups treated with Examples 29 and 21 were somewhat high in growth rate. The group treated with Example 21 was statistically high in liver weight (P<0.05), and there was no difference between testicular weights of the treated groups. Meanwhile, in sperm motility indexes divided into five grades, the groups treated with Examples 21, 29 and 57 were statistically high compared to the control (P<0.05). Population showing a motility index of more than 5' was not completely present in the control, whereas it was found to be 5, 7 and 8 in the groups treated with Examples 21, 29 and 57, respectively. Meanwhile, any lesion was not exhibited under pathological tissue conditions of liver and testicle. These test results are shown in Table 2 below.

TABLE 2

| Measured items | Test groups | | | |
|---|---|---|---|---|
| (n − 10) | Control | Example 21 | Example 29 | Example 57 |
| Starting body weight (g) | 105.9 ± 16.5 | 102.8 ± 20.6 | 99.4 ± 9.6 | 101.2 ± 10.1 |
| End body weight (g) | 336.1 ± 28.7 | 345.5 ± 56.5 | 350.2 ± 18.7 | 362.0 ± 45.5 |
| Growth rate | 3.85 ± 0.70 | 3.98 ± 0.59 | 4.24 ± 0.48 | 4.47 ± 0.45 |
| Liver weight (g) | 3.03 ± 0.24 | 3.09 ± 0.19 | 2.80 ± 0.19 | 2.79 ± 0.17 |
| Testicular weight (g) | 0.965 ± 0.057 | 0.977 ± 0.147 | 0.961 ± 0.070 | 0.910 ± 0.103 |
| Sperm motility | 4.3 ± 0.6 | 4.9 ± 0.2 | 5.0 ± 0.0 | 4.9 ± 0.2 |
| Motility index of more than 5' | 0 | 5 | 7 | 8 |
| Sperm concentration | 15.07 ± 1.84 | 15.44 ± 1.68 | 14.31 ± 1.91 | 14.75 ± 1.83 |

From the results of Table 2 above, it was confirmed that the liver weight and the sperm motility have a statistical significance (P<0.05). Also, it was found that supply of the natural tea drinks of Examples 21, 29 and 57 of the present invention to the test white rats for 9 weeks exhibits a sperm motility index significantly higher than that of the control group.

Teat Example 3

In order to measure a stamina increasing effect resulted from use of the natural tea of the present invention (Example 29), the natural tea was drunk by 30 males in their forties to sixties, in every morning and evening, for 30 days, at 140 cc each time, and examined for satisfiability and coitus number. The results are shown in Tables 3 and 4 below.

TABLE 3

Sustained time of coitus between man and wife (average value)

| Time | 1–5 min. | 5–10 min. | 10–20 min. | 20–30 min. | More than 30 min. | Un-known | Total (persons) |
|---|---|---|---|---|---|---|---|
| Before drinking | 6 | 10 | 8 | 4 | 1 | 1 | 30 |
| After drinking | 1 | 3 | 10 | 12 | 3 | 1 | 30 |

TABLE 4

Number of coitus between man and wife (average value)

| Number | 1/minth | 2/month | 3/month |
|---|---|---|---|
| Number considered as normalcy | 14/month | 10.5/month | 8.3/month |
| Before drinking | 6/month | 6/month | 6/month |
| After drinking | 14/month | 15/month | 17/month |

It is believed that the results of Tables 3 and 4 are sufficient to recognize the effect of the natural tea of the present invention, even if the placebo effect is considered.

As apparent from the foregoing, the present invention provides the relatively inexpensive natural teas in the form of liquid natural teas, powders, segments, or concentrated extracts, in which *Rhodiola sachalinensis* and *Cuscutae Semens* and/or *Torilidis Fructus*; *Rhodiola sachalinensis* and the parasitic plant; or a mixture of the above herbs is contained, as the basic elements, to which at least one herb selected from *Alnus japonica, Salviae Radix, Polyglae Radix, schizandra* and *lycium* is added. Where the natural teas of the present invention are drunk two times one day, an excellent effect of increasing stamina can be obtained.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. Natural teas for increasing stamina, which comprise *Rhodiola sachalinensis* A. Bor as a first raw material, and at least one species selected from the group consisting of parasitic plants, *Torilidis Fructus* and *Cuscutae Semens*, as a second raw material, the raw materials for the natural teas are processed as extracts obtained by extraction with a solvent selected from the group consisting of water, ethanol and a mixture thereof.

2. The natural teas according to claim 1, in which the parasitic plants are at least one species selected from the group consisting of *Cistanche deserticola* Y. C. Ma, *Orobanche coerulescens* Steph, and *Lathraea japonica* Miq.

3. The natural teas according to claim 1, in which the first raw material is contained at 10 to 95% by weight, and the second raw material is contained at 5 to 90% by weight.

4. The natural teas according to claim 5, in which *Rhodiola sachalinensis* A. Bor as the first raw material, and at least one species selected from the group consisting of parasitic plants, *Torilidis Fructus* and *Cuscutae Semens*, as the second raw material, are powders.

5. The natural teas according to claim 3, in which *Rhodiola sachalinensis* A. Bor as the first raw material, and at least one species selected from the group consisting of parasitic plants, *Torilidis Fructus* and *Cuscutae Semens*, as the second raw material, are dried matters which is obtained after steaming.

6. The natural teas according to claim 3, in which *Rhodiola sachalinensis* A. Bor as the first raw material, and at least one species selected from the group consisting of parasitic plants, *Torilidis Fructus* and *Cuscutae Semens*, as the second raw material, are consistent extracts obtained by extraction with a solvent selected from the group consisting of water, ethanol and a mixture thereof.

7. The natural teas according to claim 1, in which the natural teas further comprise at least one species selected from *Salviae Radix, Polyglae Radix,* and *Alnus japonica,* as a third raw material.

8. The natural teas according to claim 7, in which the third raw material is contained at 5 to 85% by weight.

9. The natural teas according to claim 1, in which the natural teas further comprise schizandra and/or lycium, as a fourth raw material.

10. The natural teas according to claim 9, in which the fourth raw material is contained at 5 to 80% by weight.

11. The natural teas according to claim 2, in which *Rhodiola sachalinensis* A. Bor is a root or a total herb, and *Cistanche deserticola* Y. C. Ma is peeled.

12. A method of preparing the natural teas of claim 1 for increasing stamina, in which *Rhodiola sachalinensis* A. Bor as a first raw material, and at least one species selected from the group consisting of parasitic plants, *Torilidis Fructus* and *Cuscutae Semens,* as a second raw material, are treated with at least one means selected from the group consisting of powdering, steaming and extraction.

13. The method according to claim 12, in which the parasitic plants are at least one species selected from the group consisting of *Cistanche deserticola* Y. C. Ma, *Orobanche coerulescens* Steph, and *Lathraea japonica* Miq.

14. The method according to claim 12, which the first and second raw materials are contained at 10 to 95% by weight and at 5 to 90% by weight, respectively.

15. The method according to any of claim 12, in which the first and second raw materials are powders dried so as to have a moisture content of 5 to 20%.

16. The method according to claim 15, in which the first and second materials is dry-treated by at least one drying means selected from the group consisting of lyophilization, air dry, warm heat drying, hot air drying, infrared drying, and irradiation with electromagnetic waves.

17. The method according to any of claim 12, in which the first and second raw materials are dry-treated so as to form a consistent extract having a moisture content of more than 20%.

18. The method according to claim 17, in which the first and second materials is dry-treated by at least one drying means selected from the group consisting of lyophilization, air dry, warm heat drying, hot air drying, infrared drying, and irradiation with electromagnetic waves.

19. The method according to claim 16, in which the dry-treatment is carried out after finely chopping the first and second raw materials or after finely chopping and steaming the first and second raw materials.

20. The method according to any of claim 12, in which the first and second raw materials are in a extract form, which is obtained by extraction with an extractant selected from the group consisting of ethanol, water and a mixture thereof, after finely chopping or powdering the raw materials in their original state.

21. The method according to claim 20, in which the extractant is a mixed solvent of ethanol and water, and ethanol is removed after the extraction.

22. The method according to any of claim 12, in which the natural teas further comprise at least one species selected from *Salviae Radix, Polyglae Radix,* and *Alnus japonica,* as a third raw material.

23. The method according to claim 22, in which the third raw material is contained at 5 to 85% by weight.

24. The method according to claim 12, in which the natural teas further comprise schizandra and/or lycium, as a fourth raw material.

25. The method according to claim 24, in which the fourth raw material is contained at 5 to 80% by weight.

26. The method according to claim 23, in which the third or fourth raw material is added in a powder form.

27. The method according to claim 23, in which the third or fourth raw material is added in a liquid extract form.

* * * * *